US011208501B2

(12) United States Patent
Abel et al.

(10) Patent No.: US 11,208,501 B2
(45) Date of Patent: Dec. 28, 2021

(54) PROCESS FOR DEPLETING EPOXIDE SPECIES IN CROSSLINKED POLYSACCHARIDE GEL COMPOSITIONS AND COMPOSITIONS OBTAINED THEREBY

(71) Applicant: Merz Pharma GmbH & Co. KGAA, Frankfurt am Main (DE)

(72) Inventors: Ulrich Abel, Bad Homburg (DE); Andreas Krause, Düsseldorf (DE)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 253 days.

(21) Appl. No.: 15/772,356

(22) PCT Filed: Oct. 31, 2016

(86) PCT No.: PCT/EP2016/001813
§ 371 (c)(1),
(2) Date: Apr. 30, 2018

(87) PCT Pub. No.: WO2017/076495
PCT Pub. Date: May 11, 2017

(65) Prior Publication Data
US 2018/0282439 A1 Oct. 4, 2018

(30) Foreign Application Priority Data
Nov. 2, 2015 (EP) .................................... 15003137

(51) Int. Cl.
*C08B 37/00* (2006.01)
*A61K 8/73* (2006.01)
*C08B 37/08* (2006.01)
*A61Q 19/08* (2006.01)
*A61K 8/04* (2006.01)
*A61K 31/728* (2006.01)
*C08L 5/08* (2006.01)
*A61K 31/738* (2006.01)
*A61K 8/33* (2006.01)
*A61K 9/00* (2006.01)
*A61K 9/06* (2006.01)
*A61K 31/167* (2006.01)
*A61L 27/20* (2006.01)

(52) U.S. Cl.
CPC .......... *C08B 37/0075* (2013.01); *A61K 8/042* (2013.01); *A61K 8/33* (2013.01); *A61K 8/73* (2013.01); *A61K 8/735* (2013.01); *A61K 9/00* (2013.01); *A61K 9/06* (2013.01); *A61K 31/167* (2013.01); *A61K 31/728* (2013.01); *A61K 31/738* (2013.01); *A61L 27/20* (2013.01); *A61Q 19/08* (2013.01); *C08B 37/00* (2013.01); *C08B 37/0072* (2013.01); *C08L 5/08* (2013.01); *A61K 2800/805* (2013.01); *A61K 2800/91* (2013.01); *A61L 2300/402* (2013.01)

(58) Field of Classification Search
CPC ............ C08B 37/0075; C08B 37/0072; A61K 31/167; A61K 9/00; A61K 8/042; A61K 8/735; A61K 9/06; A61K 8/73; A61K 2800/805; A61K 2800/91; A61Q 19/08; A61L 27/20; A61L 2300/402
USPC ....................................................... 536/55.1
See application file for complete search history.

(56) References Cited

U.S. PATENT DOCUMENTS

2010/0028435 A1   2/2010   Gavard
2010/0028437 A1   2/2010   Lebreton

FOREIGN PATENT DOCUMENTS

WO       2014198406 A1      12/2014
WO   WO 2014198406 A1 *   12/2014
WO   WO 2014206701 A1 *   12/2014

OTHER PUBLICATIONS

Swan (Analytical Chemistry, vol. 26, No. 5, May 1954, pp. 878-880).*
Potwora (WQP Magazine, May 31, 2011).*
PCT International Search Report for PCT/EP2016/001813, dated Feb. 3, 2017.
Jacobsen, et al., "Highly Active Oligomeric (salen)Co Catalysts for Asymmetric Epoxide Ring-Opening Reactions," Journal of the American Chemical Society, (2001), vol. 123, No. 11: 2687-2688.
De Boulle, et al., "A Review of the Metabolism of 1,4-Butanediol Diglycidyl Ether-Crosslinked Hyaluronic Acid Dermal Fillers," Dermatologic Surgery, (2013), vol. 39, No. 12: 1758-1766.

* cited by examiner

*Primary Examiner* — Shaojia A Jiang
*Assistant Examiner* — Michael C Henry
(74) *Attorney, Agent, or Firm* — McBee Moore & Vanik IP, LLC

(57) ABSTRACT

The present invention relates to a process for depleting epoxide species in epoxy-crosslinked polysaccharide gel compositions. In addition, the present invention relates to crosslinked polysaccharide gel compositions made by said process and their use in cosmetic and therapeutic applications.

17 Claims, No Drawings

PROCESS FOR DEPLETING EPOXIDE SPECIES IN CROSSLINKED POLYSACCHARIDE GEL COMPOSITIONS AND COMPOSITIONS OBTAINED THEREBY

CROSS-REFERENCE TO RELATED APPLICATIONS

This application is a National Stage entry of International Application No. PCT/EP2016/001813, filed Oct. 31, 2016, which claims priority to European Patent Application No. 15003137.5, filed Nov. 2, 2015.

BACKGROUND

Field of the Invention

The present invention relates to a process for depleting epoxide species in epoxy-crosslinked polysaccharide gel compositions. In addition, the present invention relates to crosslinked polysaccharide gel compositions made by said process and their use in cosmetic and therapeutic applications.

Description of Related Art

Hyaluronic acid (HA) is the most widely used soft tissue filler material available today for the filling and correction of soft tissue defects in aesthetic and therapeutic medicine. HA is a naturally occurring, degradable polysaccharide composed of alternating units of D-glucuronic acid (GlcUA) and N-acetyl-D-glucosamine (GlcNAc). In the majority of commercial products, HA is covalently crosslinked to increase its in vivo persistence to about 3 to 24 months.

BDDE (1,4-butanediol diglycidyl ether) is the most commonly used crosslinking agent used to crosslink HA. It forms stable ether bonds by reaction of its terminal epoxide groups and the hydroxyl groups of the GlcUA and GlcNAc units of HA. Furthermore, it has a lower toxicity than other ether-bond forming crosslinking agents (e.g., divinylsulfone). For these reasons, BDDE is currently the "gold standard" crosslinker in the HA filler industry.

Despite its "gold standard" status, BDDE-crosslinked HA products contain free unreacted BDDE as well as partially hydrolyzed BDDE, so-called epoxydiole (EPD), in some amounts. Both these epoxide impurities contain reactive epoxide groups and are therefore generally considered toxic. Also, BDDE is even suspected of being carcinogenic. Therefore, the levels of epoxide impurities need to be limited to, e.g., a one digit ppm range (preferably <2 ppm) to fulfill current regulatory requirements set by regulatory authorities such as the Food and Drug Administration (FDA).

According to the prior art, the undesirable epoxide impurities are partially removed after the crosslinking step by dialysis. However, since epoxide impurity limits are specified at low ppm levels, the dialysis process requires several repetitions and frequent replacement of large volumes of dialysis buffer and is therefore tedious and time-consuming.

SUMMARY

In view of the above, the technical problem of the present invention is the provision of a simple and efficient process for depleting epoxide species in a crosslinked polysaccharide gel composition.

The above technical problem is solved by a combined approach of inactivation/removal of residual toxic epoxide species (e.g., free unreacted epoxide species and partial hydrolysis products thereof) remaining in the gel composition after crosslinking.

More specifically, the crosslinked polysaccharide gel composition is subjected to thermal hydrolysis, acid or base mediated hydrolysis and/or nucleophilic ring-opening. Simultaneously with or subsequently to inactivation of the epoxide groups (e.g., by heat, hydrolysis or nucleophilic addition), the resulting epoxide reaction products (as well as any other epoxide species remaining in the gel) are eliminated by purification, e.g., through dialysis. The obtained gel composition depleted in epoxide species may then be subjected to sterilization to obtain a sterile, crosslinked polysaccharide gel suitable for use as soft tissue filler.

Advantageously, the process of the present invention is shorter and less laborious as compared to conventionally used dialysis procedures and, at the same time, is capable of efficiently reducing the amount of toxic epoxide species to trace amounts.

In a first aspect, the present invention provides a process for depleting epoxide species in a crosslinked polysaccharide gel composition, the process comprising the following steps:
  (a) providing a crosslinked polysaccharide gel composition, the polysaccharide being crosslinked with a bifunctional or multifunctional epoxide crosslinker, wherein said composition comprises epoxide species resulting from the polysaccharide crosslinking process,
  (b) subjecting the crosslinked polysaccharide gel composition to one, two, three or four of sub-steps (i) to (iv):
    (i) exposing the crosslinked polysaccharide gel composition to heat to effect thermal hydrolysis of epoxide functional groups of the epoxide species,
    (ii) contacting the crosslinked polysaccharide gel composition directly or indirectly with a hydrolyzing agent to effect hydrolysis of epoxide functional groups of the epoxide species,
    (iii) contacting the crosslinked polysaccharide gel composition directly or indirectly with a nucleophilic agent to effect ring-opening of epoxide functional groups of the epoxide species, and
    (iv) contacting the crosslinked polysaccharide gel composition directly or indirectly with an adsorbing agent,
  (c) dialyzing the crosslinked gel composition either concomitantly with and/or after said one or more sub-steps (i) to (iv) to obtain a crosslinked polysaccharide gel composition depleted in epoxide species.

In another aspect, the present invention provides a crosslinked polysaccharide gel composition obtainable by the process of the present invention.

In a further aspect, the present invention provides a kit, comprising a crosslinked polysaccharide gel composition of the present invention and, optionally, instructions for use. The composition may, for example, be present in the form of a prefilled syringe that contains said crosslinked polysaccharide gel composition.

In a yet further aspect, the present invention relates to the use of the crosslinked polysaccharide gel obtainable by the process of the present invention for cosmetic applications. In particular, the crosslinked polysaccharide gel composition of the present invention may be used as a soft tissue filler composition for aesthetic applications, such as in the treatment of wrinkles and lines of the skin, glabellar lines, nasolabial folds, chin folds, marionette lines, jawlines, buccal commissures, perioral wrinkles, crow's feet, cutaneous depressions, scars, temples, subdermal support of the brows, malar and buccal fat pads, tear troughs, nose, lips, cheeks, chin, perioral region, infraorbital region, and facial asymmetries.

In yet another aspect, the present invention relates to the use of the crosslinked polysaccharide gel composition obtainable by the process of the present invention in therapy. In particular, the composition is used as soft tissue filler for augmenting, filling or replacing soft tissues in therapeutic applications. Specific therapeutic indications include, but are not limited to stress urinary incontinence, vesico-ureteral reflux, vocal fold insufficiency, and vocal fold medialization.

Preferred embodiments of the present invention are set forth in the appended dependent claims.

DETAILED DESCRIPTION OF A PREFERRED EMBODIMENT

The present invention is based on the finding that a process for depleting epoxide species as described herein is significantly shorter and less tedious than the standard dialysis process used in the art for depleting epoxide impurities, while, at the same time, being very efficient in reducing residual amounts of toxic epoxide species resulting from the crosslinking process (e.g., free unreacted epoxide crosslinkers and partial hydrolysis products thereof) to trace amounts.

In particular, it was found that the process of the present invention requires fewer repetitions of dialysis cycles and associated replacements of dialysis buffer to achieve the desired low (trace amount) level of epoxide impurities, as compared to the conventional method, thereby reducing process times and simplifying the process. Desirably, the reduced dialysis times also allow limiting the risk of unwanted excessive swelling of the gel. Ultimately, the process variability is decreased and production costs are reduced. The lower content of epoxide impurities leads to a product with superior safety profile and will therefore decrease the risk for side effects and adverse events.

In a first aspect, the present invention relates to a process for depleting epoxide impurities in a crosslinked polysaccharide gel composition, the process comprising the following steps:
  (a) providing a crosslinked polysaccharide gel composition having preferably a pH of 6.5 to 7.5 or 6.8 to 7.4, the polysaccharide being crosslinked with a bifunctional or multifunctional epoxide crosslinker, wherein said composition comprises epoxide species resulting from the polysaccharide crosslinking process,
  (b) subjecting the crosslinked polysaccharide gel composition to one, two, three or four of sub-steps (i) to (iv):
    (i) exposing the crosslinked polysaccharide gel composition to heat to effect thermal hydrolysis of epoxide functional groups of the epoxide species,
    (ii) contacting the crosslinked polysaccharide gel composition directly or indirectly with a hydrolyzing agent to effect hydrolysis of epoxide functional groups of the epoxide species,
    (iii) contacting the crosslinked polysaccharide gel composition directly or indirectly with a nucleophilic agent to effect ring-opening of epoxide functional groups of the epoxide species, and
    (iv) contacting the crosslinked polysaccharide gel composition directly or indirectly with an adsorbing agent,
  (c) dialyzing the crosslinked gel composition either concomitantly with and/or after said one or more sub-steps (i) to (iv) to obtain a crosslinked polysaccharide gel composition depleted in epoxide species.

As used herein, the term "depletion" is intended to broadly refer to any means resulting in a decrease of the level of epoxide functional groups in the crosslinked polysaccharide gel composition and includes, for example, decomposition, inactivation and/or removal of epoxide functional groups.

The term "gel" or "hydrogel", as used herein, generally refers to a water-swollen three-dimensional network consisting of covalently cross-linked polymer chains. Within the present invention, the gel is preferably a cohesive gel, i.e. a gel having the capacity not to dissociate, because of the affinity of its polymer chains for each other. Cohesivity is a key characteristics of gels or hydrogels suited for use as implants and considered necessary for the solid and fluid phases of a gel to remain intact, and thus for gel integrity.

The term "polysaccharide", as used herein is not particularly limited and includes, for example, natural polysaccharides such as glycosaminoglycans (GAGs). Specific examples of suitable polysaccharides include, but are not limited to, cellulose and cellulose derivatives (e.g., carboxylated cellulose and carboxylated cellulose derivatives, such as carboxymethylcellulose, carboxyethylcellulose, carboxymethylethylcellulose), dextrane, carboxymethyldextran, carboxymethylstarch, alginate, pectin, chitin, chondroitin sulfate, dermatan sulfate, keratan, keratan sulfate, heparin, heparin sulfate, heparosan, hyaluronic acid, chitosan, carrageenan, xanthan, and mixture thereof. Preferably, the polysaccharide is selected from the group consisting of hyaluronic acid (HA), heparosan or its salts, and mixtures thereof.

As used herein, the term "crosslinker" refers to a compound having at least two functional groups (i.e. two, three or more epoxide functional groups) capable of reacting with polysaccharide polymers (e.g., hyaluronic acid) to form covalent (intra- and/or intermolecular) crosslinks. The term "bifunctional", as used herein, refers to a crosslinker having two functional groups (e.g., two epoxide functional groups) and, generally, no other reactive functionalities. The term "multifunctional", as used herein, refers to a crosslinker having at least three functional groups (e.g., at least three epoxide functional groups) and, generally, no other reactive functionalities.

Preferably, the crosslinker is a diepoxide crosslinker, e.g., 1,4-butanediol diglycidyl ether (BDDE). Other suitable diepoxid crosslinkers include, but are not limited to ethylene glycol diglycidyl ether (EGDGE), 1,6-hexanediol diglycidyl ether, polyethylene glycol diglycidyl ether, polypropylene glycol diglycidyl ether, polytetramethylene glycol digylcidyl ether, neopentyl glycol digylcidyl ether, polyglycerol polyglycidyl ether, 1,2,7,8-diepoxyoctane, 3-(bis(glycidoxymethyl)-methoxy)-1,2-propanediol, 1,4-cyclohexanedimethanol diglycidyl ether, 4-vinyl-1-cyclohexene diepoxide, 1,2,5,6-diepoxycyclooctane, and bisphenol A diglycidyl ether.

By the term "epoxide functional group", as used herein, is meant a cyclic ether with a three-atom ring, and by "epoxide" or "epoxide compound" is generally meant a compound containing at least one epoxide functional group. The term "epoxide species", as used herein, means any compound, molecule or agent, in its free or bound state (e.g., bound to a polysaccharide of the gel composition, such as HA) having at least one epoxide functional group. Epoxide species are generally undesirable in the polysaccharide gel compositions of the present invention due to their reactivity and toxicity, and are therefore sometimes referred to herein as "impurities" or "epoxide impurities".

Within the present invention, the epoxide species may be selected from unreacted (i.e. "free") epoxide crosslinkers (bifunctional or multifunctional), partial hydrolysis products of said epoxide crosslinkers (i.e. epoxydioles), and pending epoxides. An "unreacted epoxide crosslinker" means a crosslinker having all its epoxide groups in an unreacted state. The term "pending epoxide" is intended to refer to an epoxide crosslinker having incompletely reacted with the polysaccharide of the gel to form an unilateraly (or mono-linked) crosslinker where at least one of the epoxide functional groups forms a covalent bond with the polysaccharide and at least one epoxide functional group remains intact.

The term "partial hydrolysis product of an epoxide cross-linker", as used herein, means any hydrolysis product of an epoxide crosslinker having at least one epoxide functional group converted into a "diol" moiety by hydrolysis and having at least one epoxide functional group remaining intact in an unreacted state such as, e.g., an epoxydiol (EPD). By "epoxydiol" is thus meant any compound having at least one epoxide functional group and at least one moiety with two hydroxyl groups generated by hydrolysis of an epoxide functional group. For example, in case of a bifunctional epoxide crosslinker (e.g., BDDE), the reaction with water of only one of the two epoxide functional groups leads to ring opening and the formation of the corresponding epoxydiol (e.g., oxiranyl-$CH_2$—O—$(CH_2)_4$—O—$CH_2$—CH(OH)—$CH_2$OH in case of BDDE).

The term "hydrolyzing agent", as used herein, means any agent that promotes, facilitates, effects, allows or enables the decomposition, or inactivation, of epoxide species (or "epoxide impurities") by cleavage of a C—O bond through addition of water to open the epoxide ring. As used herein, the term "hydrolyzing agent" may include Lewis acids and Bronsted acids and bases, wherein said Lewis acids and Bronsted acids and bases are generally water stable. Preferably, the hydrolyzing agent is a Lewis acid or a Bronsted acid, in particular a Bronsted acid.

Suitable hydrolyzing agents for use within the present invention are selected from the group consisting of lanthanide triflates (e.g., ytterbium triflate), phosphoric acid, aluminum chloride, Ti(iOPr)$_4$, amberlyst resin, montmorillonit, poly(4-vinylpyridinium p-toluenesulfonate (PPTS), solid phase bound PPTS, Jacobsen's SalenCo(II) catalyst, microsomal epoxide hydrolase, soluble epoxide hydrolase, and mixtures thereof.

The term "nucleophilic agent", as used herein, is intended to broadly refer to a molecule that donates an electron pair to an electrophile to form a chemical bond in a chemical reaction. Within the context of the present invention, the term "nucleophilic agent" is intended to exclude water or water molecules in order to distinguish hydrolysis, which involves the nucleophilic addition of water to the epoxide (i.e. water is the nucleophile), from nucleophilic attack by, or nucleophilic addition of, other (non-water) nucleophilic agents.

Nucleophilic addition to an epoxide can be either base- or acid-catalyzed. Under acidic conditions, the position of the nucleophilic attack may be affected by carbocationic stability (as normally seen for $S_N1$ reactions). As a rule, the epoxide is first protonated, following by attack of the nucleophile, and then deprotonation. Under basic conditions, the nucleophile generally attacks the least substituted carbon, followed by protonation of the generated alkoxide (RO$^-$), in accordance with conventional $S_N2$ nucleophilic addition reaction.

Suitable nucleophilic agents may include thiol nucleophiles, alcohol nucleophiles, and amine nucleophiles. Preferably, the nucleophilic agent is a thiol nucleophilic agent. Examples of suitable thiol nucleophilic agents for use herein include, but are not limited to, soluble nucleophilic agents, such as acetylcysteine, sodium sulfite, sodium thiosulfate, glutathione, thiourea, and solid phase nucleophilic agents, such as thiol-modified polymer resins (e.g., QuadraPure DET), thiol-modified silica (e.g., QuadraSil MP), thiourea-modified polymer resins (e.g., QuadraPure TU), thiourea-modified silica (e.g., QuadraSil MTU), and any mixture of one or more of said soluble nucleophilic agents and/or one or more of said solid phase nucleophilic agents.

Suitable absorbing agents for use herein include agents that have a high ability to absorb free (i.e. unbound) epoxide species on its outer and/or inner (e.g., pore) surfaces. Examples of suitable absorbing agents include, but are not limited to, charcoal, activated charcoal, zeolite (e.g., zeolite ZSM-5, zeolite beta, zeolite Y), mordenite, and mixtures thereof.

In step (a) of the process of the present invention, the provided gel composition is not limited to any particular polysaccharide and may be selected from the polysaccharides mentioned herein above. Preferably, as also mentioned above, the polysaccharide is selected from the group consisting of hyaluronic acid (HA), heparosan, and mixtures thereof, and most preferred the polysaccharide is hyaluronic acid. As used herein, the term "hyaluronic acid" or "HA" includes hyaluronic acid, hyaluronate, and any hyaluronate salt such as sodium hyaluronate. Furthermore, the polysaccharide may be present in the gel composition at a concentration of between 1.0 mg/ml and 50 mg/ml, preferably between 5.0 mg/ml and 30 mg/ml, and more preferably between 10.0 mg/ml and 25 mg/ml.

Within the context of the present invention, the cross-linked polysaccharide provided in step (a) may comprises hyaluronic acid and one or more polysaccharides other than HA and/or heparosan in an amount of less than 10 wt. %, preferably less than 5 wt. %, more preferably less than 1.0 wt. %, based on the total weight of all polysaccharides present in the composition.

Moreover, the crosslinked polysaccharide gel composition provided in step (a) is not limited to a particular crosslinking degree. For example, in case of BDDE-crosslinked hyaluronic acid, the degree of modification, expressed as the ratio of the sum of mono- and double-linked BDDE-crosslinkers to the sum of HA disaccharide units, may be in the range of about 0.2% to about 25%, preferably in the range of 2% to 15%, as measured by NMR in accordance with the method described in Edsman et al. (Dermatol. Surg. 2012, 38:1170-1179), Guarise et al. (Carbohydrate Polymers 2012, 88:428-434), and Kenne et al. (Carbohydrate Polymers 2013, 91:410-418). Also, the crosslinking degree may vary within the gel as in case of polydensified hyaluronic acid gels. Furthermore, the molecular weight of the polysaccharide is not particularly limited and, in case of hyaluronic acid, may be in the range of 0.2 MDa to 5 MDa, e.g., from 0.5 MDa to 3 MDa, as determined for example by the Mark-Houwink equation [$\eta$]=K×M$^a$ ([$\eta$]=intrinsic viscosity in m$^3$/kg measured as defined in European Pharmacopoeia 7.0; Hyaluronic Acid monograph No. 1472, January 2011), M=molecular weight, K=2.26×10$^{-5}$, and a=0.796), and include HAs of different molecular weights, e.g., a low molecular weight HA and a high molecular weight HA.

In step (b) of the process according to the present invention, the crosslinked polysaccharide gel composition is subjected to one, two, three or four of sub-steps (i) to (iv). Preferably, the gel is subjected to one, two, three or four of sub-steps (i) to (iv) at a pH of 6.5 to 7.5 or 6.8 to 7.4. Furthermore, the thermal hydrolysis of sub-step (i) is preferably carried out by heating the gel composition (e.g., by hot air, such as in an oven, or by hot water, such as in a water bath, or by direct heating, such as on a heating plate) in a container or vessel made of any suitable material, e.g., any kind of glass, Teflon or plastic. The gel composition, which is usually physiologically buffered and/or is preferably pH neutral (e.g., has a pH of about 6.5 to 7.5, particularly 6.8 to 7.4), is preferably subjected to thermal treatment for 0.25 h to 18 h, particularly for 0.5 h to 12 h, more particularly for 1 h to 6 h, at a temperature of between 40° C. and 120° C., particularly between 50° C. and 100° C., and more particularly between 60° C. and 80° C.

Sub-steps (ii) and (iii) of step (b) of the process according to the present invention are preferably carried out as described in detail below with respect to the second, third and fourth preferred embodiments of the process according to the present invention (see steps (b"), (b'"), and (b""))

The term "directly", as used herein, means that the hydrolyzing agent and the nucleophilic agent, respectively, are added to, and typically mixed with, the crosslinked polysaccharide gel composition, i.e. that the polysaccharide molecules of the gel composition come into physical contact with the hydrolyzing agent and/or the nucleophilic agent. In contrast, the term "indirectly", as used herein, means that the hydrolyzing agent and the nucleophilic agent, respectively, do not come into direct contact with each other but are physically separated, such as by the use of a semi-permeable dialysis membrane. Generally, the semi-permeable dialysis membrane allows the soluble hydrolyzing and nucleophilic agent molecules to go through the dialysis membrane into the inside of the dialysis bag where the crosslinked polysaccharide gel composition is situated.

In one preferred (first) embodiment, the process of the present invention comprises the following steps:
(a) providing a crosslinked polysaccharide gel composition, preferably at a pH of 6.5 to 7.5 or 6.8 to 7.4, comprising epoxide species as described herein above,
(b') exposing the crosslinked polysaccharide gel composition to heat to effect thermal hydrolysis of the epoxide functional groups of the epoxide species, and
(c') dialyzing the heat-treated composition of (b') to obtain a crosslinked polysaccharide gel composition depleted in epoxide species.

The thermal treatment of step (b') is preferably carried out by heating the gel composition (e.g., by hot air, such as in an oven, or by hot water, such as in a water bath, or by direct heating, such as on a heating plate) in a container or vessel made of any suitable material, e.g., any kind of glass, Teflon or plastic.

The gel composition, which is usually physiologically buffered and/or is preferably pH neutral (e.g., has a pH of about 6.5 to 7.5 or 6.8 to 7.4) may be subjected to thermal treatment for 0.25 h to 18 h, particularly for 0.5 h to 12 h, more particularly for 1 h to 6 h, at a temperature of between 40° C. and 120° C., particularly between 50° C. and 100° C., and more particularly between 60° C. and 80° C.

The dialysis is typically carried out at a temperature of 3° C. to 40° C., preferably at a temperature of 10° C. to 25° C. (in case of separate heat treatment and dialysis steps). The dialysis buffer is usually replaced several times, as known in the art. The dialysis membrane used has preferably a molecular weight cut-off of between 5 kDa and 30 kDa, for example 12-14 kDa, and may be made of regenerated cellulose (RC). The dialysis membrane is usually a dialysis tube (e.g., with a 45 mm width and a diameter of 29 mm) closed at both sides by suitable mechanical means.

It is contemplated within the scope of the present invention that steps (b') and (c') can be carried out concomitantly (e.g., by carrying out the dialysis with a heated dialysis buffer at a temperature of, for example, 30° C. to 85° C., in particular 40° C. to 80° C. or 50° C. to 70° C.) or that step (c') is a separate step that follows step (b'). Furthermore, it is also contemplated that the process according to this first preferred embodiment comprises further steps, in particular steps (b") and optionally (c"), steps (b'") and optionally (c'"), and/or steps (b"") and optionally (c""), wherein the process may comprise only one dialysis step or wherein two, three or four of steps (c'), (c"), (c'"), and (c"") are combined in one dialysis step.

A specific example of a process in accordance with this first preferred embodiment comprises heating 400 ml of an epoxy-crosslinked polysaccharide gel composition in physiological phosphate buffer in a 750 ml glass cartridge in an oven for 3 h at 70° C., and then subjecting the heat-treated gel composition to dialysis.

In another preferred (second) embodiment, the process of the present invention comprises the following steps:
(a) providing a crosslinked polysaccharide gel composition, preferably at a pH of 6.5 to 7.5 or 6.8 to 7.4, comprising epoxide species as defined herein above,
(b") adding a hydrolyzing agent and/or a nucleophilic agent directly to the crosslinked polysaccharide gel composition to effect hydrolysis or nucleophilic ring opening of the epoxide functional groups of the epoxide species, and
(c") dialyzing the composition of (b") to obtain a crosslinked polysaccharide gel composition depleted in epoxide species.

The addition of a hydrolyzing agent and/or a nucleophilic agent to the gel composition in accordance with step (b") results in the epoxide ring-opening and, thus, inactivation of residual epoxide species. The at least one hydrolysis agent and/or at least one nucleophilic agent may be added singly or in any combination, preferably, in the form of one or more aqueous solutions, optionally buffered, to the gel composition placed in a vessel or container made of any suitable material, e.g., any kind of glass, Teflon or plastic. Preferably, the hydrolyzing agent and the nucleophilic agent are defined as herein above.

The at least one hydrolysis agent and/or at least one nucleophilic agent is (are) preferably added to the gel composition such that the total amount in the resulting gel composition is in the range of 0.05% to 10% by weight/volume, more preferably in the range of 0.1% to 5% by weight/volume, particularly preferably in the range of 0.5% to 3% by weight/volume, and most preferably in the range of 1% to 2% by weight/volume. Typically, an aqueous solution of the at least one hydrolysis agent and/or at least one nucleophilic agent is added to the hydrogel composition in a ratio of 1:10. The resulting gel composition is preferably treated at a temperature ranging from room temperature (e.g., 20° C. or 25° C.) to 80° C., particularly from 30° C. to 50° C., for 15 min to 20 h, preferably from 30 min to 12 h, more preferably from 1 h to 6 h.

The dialysis is typically carried out at a temperature of 3° C. to 80° C., 3° C. to 60° C. or 3° C. to 40° C., preferably at a temperature of 10° C. to 25° C. (in case of separate heat treatment and dialysis steps). The dialysis buffer is usually replaced several times, as known in the art. The dialysis membrane used has preferably a molecular weight cut-off of between 5 kDa and 30 kDa, for example 12-14 kDa, and may be made of regenerated cellulose (RC). The dialysis membrane is usually a dialysis tube (e.g., with a 45 mm width and a diameter of 29 mm) closed at both sides by suitable mechanical means.

It is contemplated within the scope of the present invention that steps (b") and (c") can be carried out concomitantly or, more preferably, that step (c") is a separate step that follows step (b"). Furthermore, it is also contemplated that the process according to this second preferred embodiment comprises further steps, in particular steps (b') and optionally (c'), steps (b''') and optionally (c''') and/or steps (b'''') and optionally (c''''), wherein the process may comprise only one dialysis step or wherein two, three or four of steps (c'), (c"), (c'''), and (c'''') are combined in one dialysis step.

A specific example of a process in accordance with this second embodiment comprises adding 40 ml of an aqueous solution, comprising purified water or an aqueous physiological buffer solution containing 2 g to 5 g of a hydrolyzing agent and/or nucleophilic agent, to 400 ml of an epoxy-crosslinked polysaccharide gel in a reaction vessel, and treating the mixture for 30 min to 12 h (e.g., 2 h) at 80° C.

In a further preferred (third) embodiment, the process of the present invention comprises the following steps:
(a) providing a crosslinked polysaccharide gel composition, preferably at a pH of 6.5 to 7.5 or 6.8 to 7.4, comprising epoxide species as defined herein above,
(b''') adding a hydrolyzing agent and/or a nucleophilic agent into a dialysis buffer, wherein both the hydrolyzing agent and the nucleophilic agent are not solid phase supported, or wherein the hydrolyzing agent or the nucleophilic agent is solid phase supported, or wherein both the hydrolyzing agent and the nucleophilic agent are solid phase supported, and
(c''') dialyzing the crosslinked polysaccharide gel composition against the dialysis buffer of (b'''), wherein the solid phase supported hydrolyzing agent and the solid phase supported nucleophilic agent do not come into direct contact with the crosslinked polysaccharide gel composition, to obtain a crosslinked polysaccharide gel composition depleted in epoxide species.

The depletion of residual epoxide species in this embodiment is generally achieved by reaction of epoxide functional groups with a hydrolyzing agent and/or a nucleophilic agent, resulting in epoxide inactivation, and removal of any reaction products and unreacted epoxide species by dialysis. The hydrolyzing agent and the nucleophilic agent may be either both water-soluble or water-insoluble (i.e. solid phase supported), or the hydrolyzing agent may be water-soluble and the nucleophilic agent may be water-insoluble, or vice versa. As explained above, the water-soluble agents (hydrolyzing and/or nucleophilic agents) are generally capable of passing the dialysis membrane, whereas the solid phase supported agents cannot go through the dialysis membrane. Preferably, the hydrolyzing agent and the nucleophilic agent are defined as herein above.

The at least one hydrolysis agent and/or at least one nucleophilic agent may be present in the dialysis buffer (e.g., an aqueous solution of purified (distilled) water or an aqueous physiological buffer solution) in an amount of form 0.001% to 3% by weight/volume (in case of solid phase supported hydrolyzing agent/nucleophilic agent also up to 5% by weight/volume), preferably from 0.05% to 2.0% by weight/volume, more preferably from 0.1% to 1% by weight/volume. The volume of the dialysis buffer to the volume of hydrogel composition to be dialyzed may be, for example, about 10:1.

The dialysis is typically carried out at a temperature of 3° C. to 70° C., preferably 3° C. to 50° C., and more preferably 3° C. to 25° C. The dialysis buffer is usually replaced several times (e.g., 6 to 9 times), as known in the art. The dialysis membrane used has preferably a molecular weight cut-off of between 5 kDa and 30 kDa, for example 12-14 kDa, and may be made of regenerated cellulose (RC). The dialysis membrane is usually a dialysis tube (e.g., with a 45 mm width and a diameter of 29 mm) closed at both sides by suitable mechanical means.

Furthermore, it is also contemplated that the process according to this third preferred embodiment comprises further steps, in particular steps (b') and optionally (c'), steps (b") and optionally (c"), and/or steps (b'''') and optionally (c''''), wherein the process may comprise only one dialysis step or wherein two, three or four of steps (c'), (c"), (c'''), and (c'''') are combined in one dialysis step.

A specific example of a process in accordance with this third embodiment comprises the steps of providing 4000 ml of an aqueous physiological buffer solution containing 5 g hydrolyzing agent and/or nucleophilic agent (in case of water-soluble agents) or 15 g hydrolyzing agent and/or nucleophilic agent (in case of solid phase supported agents), and using the resulting dialysis buffer to dialyze 400 ml of an epoxy-crosslinked polysaccharide gel composition in a dialysis membrane (tube or bag) at a temperature of 3° C. to 23° C. for 15 h to 50 h (with buffer change about every 4 h).

In a yet further preferred (fourth) embodiment, the process of the present invention comprises the following steps:
(a) providing a crosslinked polysaccharide gel composition, preferably at a pH of 6.5 to 7.5 or 6.8 to 7.4, comprising epoxide species as defined herein above,
(b'''') adding a solid state absorbing agent into a dialysis buffer, and
(c'''') dialyzing the crosslinked polysaccharide gel composition against the dialysis buffer of (b'''') without direct contact between the solid state absorbing agent and the crosslinked polysaccharide gel composition to obtain a crosslinked polysaccharide gel composition depleted in epoxide species.

In this embodiment, the depletion of the epoxide species is effected by treatment of the gel composition during dialysis with a solid state absorbing agent. As noted above, a "solid state absorbing agent" within the meaning of the present invention refers to an absorbing agent that does not dissolve in an aqueous solution but is present in a solid state or, put in other words, solid phase. Preferred examples of solid state absorbing agents include those mentioned above.

The dialysis is typically carried out at a temperature of 3° C. to 70° C., preferably 3° C. to 50° C., and more preferably 3° C. to 25° C. The dialysis buffer is usually replaced several times, as known in the art. The dialysis membrane used has preferably a molecular weight cut-off of between 5 kDa and 30 kDa, for example 12-14 kDa, and may be made of regenerated cellulose (RC). The dialysis membrane is usually a dialysis tube (e.g., with a 45 mm width and a diameter of 29 mm) closed at both sides by suitable mechanical means.

Furthermore, it is also contemplated that the process according to this fourth preferred embodiment comprises further steps, in particular steps (b') and optionally (c'), steps (b") and optionally (c"), and/or steps (b''') and optionally (c'''), wherein the process may comprise only one dialysis step or wherein two, three or four of steps (c'), (c"), (c'''), and (c"") are combined in one dialysis step.

A specific example of a process in accordance with this fourth embodiment comprises the provision of 4000 ml of an aqueous solution (e.g., purified water or an aqueous physiological buffer solution) containing 2 g to 500 g of a solid state absorbing agent, and using the resulting dialysis buffer to dialyze 400 ml of an epoxy-crosslinked polysaccharide gel in a dialysis membrane (tube or bag) at a temperature of 3° C. to 23° C. for 15 to 50 h (with buffer change about every 4 h).

In accordance with the present invention, the process may further comprise the following step:
  (d) sterilizing the crosslinked polysaccharide gel composition depleted in epoxide species to form a sterile, crosslinked polysaccharide gel composition suitable for use as a soft tissue filler.

The term "sterilizing", "sterilized" or "sterile", as used herein, is intended to refer to heat sterilization, in particular moist heat sterilization (e.g., steam sterilization), and preferably refers to autoclaving. Autoclaving may be carried out at a temperature of 120° C. to 132° C. for 0.3 min to 20 min, or at 121° C. to 130° C. for 0.5 min to 10 min, e.g. at 121° C. for 0.5 min to 2 min.

It is further pointed out that the pH of the crosslinked polysaccharide gel is preferably within 6.5 to 7.5, in particular 6.8 to 7.4, throughout the process of the present invention. In other words, any treatment of the gel and subsequent or concomitant dialysis is preferably carried out in said pH range. Furthermore, if additional components are added, the pH may be adjusted to a suitable range before or after said addition such that the pH of the gel is within the above-mentioned range. In particular, before the final sterilization step, the crosslinked polysaccharide gel generally has a pH within the stated range.

Furthermore, the process of the present invention may further include a step of adding non-crosslinked polysaccharides, in particular non-crosslinked HA, non-crosslinked heparosan, non-crosslinked carboxymethyl cellulose (CMC), and mixture thereof, to result in a total non-crosslinked polysaccharide amount in the final product of, preferably, less than 5.0 mg/ml, more preferably less than 3.0 mg/ml, and most preferably less than 2.0 mg/ml.

Within the present invention, it is also contemplated that the process may further comprise a step of:
  adding a local anesthetic agent such as lidocaine, and/or one or more additional compounds selected from polyols, vitamins, alkali metal and alkaline earth metal salts, metals, antioxidants, anesthetic agents, amino acids, ceramic particles, cells (e.g., stem cells and adipocytes), fat, lipids, growth factors, cytokines, and small molecule drugs.

Within the context of the present invention, the addition of a local anesthetic is particularly desirable in view of its ability to mitigate pain upon injection. Exemplary local anesthetic agents include, but are not limited to, local anesthetic agents of the "caine-type", such as ambucaine, amylocaine, benzocaine, betoxycaine, bupivacaine, butacaine, butanilicaine, butoxycaine, carticaine, chloroprocaine, cyclomethycaine, dibucaine, dimethocaine, etidocaine, beta-eucaine, formocaine, hexylcaine, hydroxytetracaine, leucinocaine mesylate, lidocaine, mepivacaine, meprylcaine, metabutoxycaine, myrtecaine, naepaine, octocaine, orthocaine, oxethazaine, parethoxycaine, phenacaine, piperocaine, piridocaine, prilocaine, procaine, propanocaine, proparacaine, propipocaine, propoxycaine, pseudococaine, pyrrocaine, ropivacaine, tetracaine, tolycaine, trimecaine, and salts thereof. The "caine-type" anesthetics may be added such that they are present in the final crosslinked polysaccharide gel composition in a total amount of, e.g., 0.05 wt. % to 8.0 wt. %, 0.1 wt. % to 4.0 wt. %, 0.2 wt. % to 3.0 wt. %, 0.3 wt. % to 2.0 wt. %, or 0.4 wt. % to 1.0 wt. %. Preferably, the anesthetic agent is lidocaine, such as in the form of lidocaine hydrochloride, in particular in the amounts as indicated above.

Suitable polyols for use herein include, but are not limited to, glycerol, mannitol, sorbitol, propylene glycol, erythritol, xylitol, maltitol, and lactitol. Particularly suitable for use herein is mannitol and glycerol. Further, the polyol is preferably glycol, optionally in combination with one or more of the aforementioned polyol compounds, in particular mannitol. Suitable vitamins include vitamin C, vitamin E and vitamins of the B group, i.e. one or more of $B_1$, $B_2$, $B_3$, $B_5$, $B_6$, $B_7$, $B_9$ and $B_{12}$ vitamins. The vitamins may be present to stimulate and maintain cellular metabolism and, thus, to promote collagen production. Particularly preferred for use here is vitamin C, vitamin E and vitamin $B_6$. A suitable salt for use herein is a zinc salt, and the ceramic particles are preferably hydroxyapatite particles, e.g., calcium hydroxyl apatite (CaHA) particles.

In another aspect, the present invention relates to a crosslinked polysaccharide gel composition obtainable by the process of the present invention.

A preferred crosslinked polysaccharide gel composition is a crosslinked hyaluronic acid gel optionally containing a local anesthetic agent like lidocaine. Furthermore, the crosslinked polysaccharide gel composition is preferably sterile, in particular sterilized by heat sterilization, especially sterilized by heat sterilization (e.g., autoclaving), as described herein.

The composition has preferably a total residual amount of epoxide species of less than 10 ppm, more preferably less than 5 ppm, most preferably less than 2 ppm. Further, the composition has typically a storage modulus (G') at 1 Hz of between about 10 Pa and 2000 Pa, a tan δ at 1 Hz of between 0.01 and 5.0, and an extrusion force, as measured through a needle of 27 G½ at a rate of 12.5 mm/min using a standard 1 ml glass syringe, of between 2 and 100 N.

In a further aspect, the present invention relates to a kit, comprising a composition according to the present invention and, optionally, instructions for use. Preferably, the composition is present in the form of a prefilled syringe prefilled with said composition. The composition is generally sterile and is usually sterilized as described herein before. Conveniently, the prefilled syringe may be sterilized as a whole to obtain a ready-to-use prefilled syringe.

In a yet further aspect, the present invention relates to the use of the composition according to the invention for cosmetic applications, in particular as a dermal filler for cosmetic applications. In accordance with the present invention, the cosmetic applications may include, but are not limited to, the treatment of wrinkles and lines of the skin, glabellar lines, nasolabial folds, chin folds, marionette lines, jawlines, buccal commissures, perioral wrinkles, crow's feet, cutaneous depressions, scars, temples, subdermal support of the brows, malar and buccal fat pads, tear troughs, nose, lips, cheeks, chin, perioral region, infraorbital region, and facial asymmetries.

In yet another aspect, the present invention relates to a composition according to the invention for use in therapy, in particular for use as a soft tissue filler in therapy, for example for use in the treatment of stress urinary incontinence, vesico-ureteral reflux, vocal fold insufficiency, and vocal fold medialization. The term "soft tissue filler", as used herein, generally refers to a material designed to add volume to areas of soft tissue deficiency. This includes, e.g. augmenting, filling or replacing soft tissues.

The present invention will now be further illustrated by the following, non-limiting examples.

EXAMPLES

The examples provided below demonstrate the ability of the process according to the present invention to reduce (deplete) the level of unwanted epoxide species in epoxy-crosslinked polysaccharide gels.

Example 1

Epoxide Depletion Capacity of Solid State Absorbing Agents

A freshly prepared solution of EPD 3-(4-(oxiran-2-yl-methoxy)butoxy)propane-1,2-diol (conc.=100 ppm) in PBS buffer (10 mM) was stirred at room temperature in the presence of solid state absorbing agents as scavengers (10-fold excess by weight vs. EPD). Samples were taken at 1 h, 6 h and 24 h, and their remaining contents of EPD in ppm were determined for each time point by high performance liquid chromatography (HPLC). The results are shown in Table 1.

TABLE 1

| | Content of EPD (in ppm relative to the initial EPD conc. of 100 ppm) | | | | | |
|---|---|---|---|---|---|---|
| Time (h) | Zeolite Beta | Quadra-Pure TU | QuadraSil MTU | Zeolite ZSM-5 | Mordenite | Zeolite Y |
| 0 | 100 | 100 | 100 | 100 | 100 | 100 |
| 1 | 0 | 64 | 78 | 0 | 0 | 33 |
| 6 | 0 | 28 | 72 | 0 | 0 | 30 |
| 24 | 0 | 3 | 53 | n.d. | n.d. | n.d. |

Example 2

Epoxide Depletion Capacity of Thiol Nucleophiles

A freshly prepared solution of EPD (40 µM) in deuterated PBS buffer (10 mM) was stirred at room temperature in the presence of thiol nucleophiles as scavengers (2-fold excess related to EPD). Samples were taken at 0 h (i.e. immediately after addition), 2 h, 8 h and 16 h, and analyzed for their EPD contents by $^1$H NMR. The results are shown in Table 2.

TABLE 2

| Content of EPD (in % relative to the initial EPD conc. of 100%) | | | |
|---|---|---|---|
| Time (h) | Na-thiosulfate | Thiourea | Acetylcystein |
| 0* | 91 | 91 | 92 |
| 2 | 13 | 62 | 87 |
| 8 | 0 | 29 | 60 |
| 16 | 0 | 8 | 55 |

*immediately after EPD addition

Example 3

Epoxide Depletion by Thermal Hydrolysis

A freshly prepared solution of EPD (conc.=100 ppm) in PBS buffer (10 mM) was stirred at temperatures of 20° C., 40° C. and 60° C. Samples were taken at 1 h, 6 h and 24 h, and their remaining content of EPD was measured by HPLC in duplicates for each time point. The results are shown in Table 3.

TABLE 3

| Content of EPD (in ppm relative to the initial EPD conc. of 100 ppm) | | | |
|---|---|---|---|
| Time (h) | at T = 20° C. | at T = 40° C. | at T = 60° C. |
| 0 | 100 | 100 | 100 |
| 1 | 97 | 94 | 87 |
| 6 | 95 | 88 | 57 |
| 24 | 88 | 67 | 22 |

Example 4

Preparation of a HA Filler Depleted in Epoxide Species 10 g of hyaluronic acid (HA; $M_w=2\times10^6$ Da) were diluted in 100 ml of a NaOH solution at 1%. The mixture was homogenized until a transparent solution was obtained. The crosslinking reaction was initiated by addition of 950 µl of 1,4-butanediol diglycidyl ether (BDDE). It was mixed for 1 h at 25° C. followed by heating at 50° C. for 4 h in a sealed vessel. The reaction was then stopped by addition of phosphate buffer solution containing HCl to obtain a pH between 6.6-7.4 followed by homogenization for 24 h.

Next, the homogenized gel composition was directly treated via heat, hydrolysis or nucleophilic agents, absorbers, etc. The gel obtained is then dialyzed for 24 h (regenerated cellulose, separation limit: MW=12-14 kDa) against a buffered solution at pH=7 (Gel I) in accordance with WO 2005/085329 A1. Alternatively, the aqueous dialysis medium was treated with heat, hydrolysis or nuclophilic agents, absorbers etc. in accordance with WO 2005/085329 A1. The final gel has a hyaluronic acid content of 2.5% by mass.

The invention claimed is:

1. A process for depleting epoxide species in a crosslinked polysaccharide gel composition, the process comprising:
    (a) providing a crosslinked polysaccharide gel composition having a pH of 6.5 to 7.5, the polysaccharide being crosslinked with a bifunctional or multifunctional epoxide crosslinker, wherein said composition comprises epoxide species resulting from the polysaccharide crosslinking process,
    (b) exposing the crosslinked polysaccharide gel composition to heat by a thermal treatment to effect thermal hydrolysis of epoxide functional groups of the epoxide species, wherein the thermal treatment is carried out for 1 h to 18 h at a temperature of 40° C. to 120° C., and
    (c) dialyzing the crosslinked gel composition either concomitantly with and/or after (b) to obtain a crosslinked polysaccharide gel composition depleted in epoxide species.

2. The process of claim 1, wherein the epoxide crosslinker is a diepoxide crosslinker.

3. The process of claim 1, wherein the crosslinked polysaccharide is selected from the group consisting of hyaluronic acid (HA), heparosan or its salts, and mixtures thereof.

4. The process of claim 1, further comprising:
(d) sterilizing the crosslinked polysaccharide gel composition depleted in epoxide species to form a sterile, crosslinked polysaccharide gel composition suitable for use as a soft tissue filler.

5. The process of claim 1, wherein the process further comprises adding a local anesthetic agent optionally lidocaine and/or one or more additional compounds selected from vitamins, polyalcohols, alkali metal and alkaline earth metal salts, metals, antioxidants, anesthetic agents, amino acids, and ceramic particles.

6. The process of claim 2, wherein the epoxide crosslinker is 1,4-butanediol diglycidyl ether (BDDE).

7. The process of claim 1, wherein the thermal treatment is carried out for 1 h to 12 h at a temperature of 50° C. to 100° C.

8. The process of claim 1, wherein the thermal treatment is carried out for 1 h to 6 h at a temperature of 60° C. to 80° C.

9. A process for inactivating epoxide species in a crosslinked polysaccharide gel composition, the process comprising:
(a) providing a crosslinked polysaccharide gel composition having a pH of 6.5 to 7.5, the polysaccharide being crosslinked with a bifunctional or multifunctional epoxide crosslinker, wherein said composition comprises epoxide species resulting from the polysaccharide crosslinking process, and
(b) exposing the crosslinked polysaccharide gel composition to heat by a thermal treatment to effect thermal hydrolysis of epoxide functional groups of the epoxide species, wherein the thermal treatment is carried out for 1 h to 18 h at a temperature of 40° C. to 120° C.

10. The process of claim 9, wherein the thermal treatment is carried out for 1 h to 12 h at a temperature of 50° C. to 100° C.

11. The process of claim 9, wherein the thermal treatment is carried out for 1 h to 6 h at a temperature of 60° C. to 80° C.

12. The process of claim 9, further comprising:
(c) dialyzing the heat-treated composition of (b) to obtain a crosslinked polysaccharide gel composition depleted in epoxide species.

13. The process of claim 9, wherein the epoxide crosslinker is a diepoxide crosslinker.

14. The process of claim 9, wherein the crosslinked polysaccharide is selected from the group consisting of hyaluronic acid (HA), heparosan or its salts, and mixtures thereof.

15. The process of claim 12, further comprising:
(d) sterilizing the crosslinked polysaccharide gel composition depleted in epoxide species to form a sterile, crosslinked polysaccharide gel composition suitable for use as a soft tissue filler.

16. The process of claim 9, wherein the process further comprises adding a local anesthetic agent optionally lidocaine and/or one or more additional compounds selected from vitamins, polyalcohols, alkali metal and alkaline earth metal salts, metals, antioxidants, anesthetic agents, amino acids, and ceramic particles.

17. The process of claim 9, wherein the epoxide crosslinker is 1,4-butanediol diglycidyl ether (BDDE).

* * * * *